United States Patent [19]

Epstein et al.

[11] Patent Number: 5,863,948
[45] Date of Patent: Jan. 26, 1999

[54] INCREASING AQUEOUS HUMOR OUTFLOW

[75] Inventors: David L. Epstein, Wayland, Mass.; Alice Cheng-Bennett, Irvine; C. Gluchowski, Mission Viejo, both of Calif.

[73] Assignee: Massachusetts Eye and Ear Infirmary, Boston, Mass.

[21] Appl. No.: 311,367

[22] Filed: Sep. 23, 1994

Related U.S. Application Data

[63] Continuation of Ser. No. 152,248, Nov. 12, 1993, abandoned, which is a continuation of Ser. No. 28,631, Mar. 5, 1993, abandoned, which is a continuation of Ser. No. 908,636, Jun. 11, 1992, abandoned, which is a continuation of Ser. No. 747,461, Aug. 12, 1991, abandoned, which is a continuation of Ser. No. 514,488, Apr. 26, 1990, abandoned, which is a continuation-in-part of Ser. No. 123,797, Nov. 23, 1987, abandoned, which is a continuation-in-part of Ser. No. 745,325, Jun. 14, 1985, abandoned.

[51] Int. Cl.$^6$ .................................................. A61K 31/19
[52] U.S. Cl. ........................................... 514/571; 514/913
[58] Field of Search ..................................... 514/571, 913

[56] References Cited

U.S. PATENT DOCUMENTS

| | | | |
|---|---|---|---|
| 3,255,241 | 6/1966 | Schultz et al. | |
| 3,324,121 | 6/1967 | Sprague | 544/130 |
| 3,342,851 | 9/1967 | Schultz et al. | 562/463 |
| 3,453,312 | 7/1969 | Sprague et al. | 514/869 |
| 4,070,539 | 1/1978 | Cragoe et al. | 514/869 |
| 4,590,210 | 5/1986 | Landham | 514/548 |
| 4,757,089 | 7/1988 | Epstein. | |
| 4,826,879 | 5/1989 | Yamamoto et al. | 514/657 |

FOREIGN PATENT DOCUMENTS

| | | |
|---|---|---|
| 883792 | 10/1971 | Canada. |
| 1141422 | 1/1967 | United Kingdom. |

OTHER PUBLICATIONS

Invest Ophthamol (Vis. Sci 226–752–6 (1982). Epstein et al.
Invest. Ophthamol. Vis. Sci 24(6) 1710 (1982). Lindenmayer et al.
Invest. Ophthamol. Vis. Sci 24(3) 1283 (1983), Kahn et al.
Invest. Ophthamol. Vis. Sci 25(3), 278 (1984), Freddo et al.
Epstein et al., "Ethacrynic Acid Uniquely Disrupts Cellular Tubulin in Trabecular and Other Endothelial Cells", Arvo Abstract (1991).
Hooshmand and Epstein, "Thiol Adducts of Ethacrynic Acid Increase Outflow Facility in Enucleated Calf Eyes", Arvo Abstract (1991).
Schroeder et al., "Topical Ethacrynic Acid Lowers Intraocular Pressure in Rabbits and Monkeys", Arvo Abstract (1991).
Gere, M., "Risk of postcataract IOP spike justified prophylactic drugs", Ocular Surgery News vol. 8, No. 14 (1990).
Koechel and Cafruny, "Thiol Adducts of Ethacrynic Acid: A Correlation of the Rate of Liberation of Ethacrynic Acid w/the Onset & Magnitude of the Diuretic Response", The Journal of Pharmacology and Experimental Therapeutics 192:179–194 (1975).

Cragoe, E.J., "The (Aryloxy)acetic Acid Family of Diuretics", J. Clin. Pharmacol. 9,577:203–223 (1980).
Liang et al., "Ethacrynic Acid Increases Facility of Outflow in the Human Eye In Vitro", Arvo Abstracts 1849 (1990).
Green and Mayberry, "Drug Effects on the Hydraulic Conductivity of the Isolated Rabbit Ciliary Epithelium", Quarterly J. Exp. Physiol. 70:271–281 (1985).
Epstein et al., "The Search for a Sulfhydryl Drug for Glaucoma", Invest. Opthalmol. Vis. Sci. 27 (Suppl. 3) 179 (1986).
D.L. Epstein et al.; N–Ethylmaleimide Increases The Facility of Aqueous Outflow of Excised Monkey and Calf Eyes; Invest. Opthalmology & Visual Scien.; 22:752–56; (Jun. 1982).
A.M. Magro et al.; Effect of Sulfhydryl–Reactive ATPase Inhibitors upon Mast Cell and Basophil Activation; Int'l Archives of Allergy and Appl. Immunology; 77:41–45; (1983).
D.L. Epstein et al.; The Effect of Diamide on Lens Glutathione and Lens Membrane Function; Invest. Ophthalmology; 9:629–38; (Aug. 1979).
J.M. Lindenmayer; Morphology and Function of the Aqueous Outflow System in Monkey Eyes Perfused with Sulfhydryl Reagents; Invest. Ophthalmology & Visual Sci.; 24:710–17; (Jun. 1983).
D.L. Epstein et al.; Effect of iodoactamide perfusion on outflow facility and metabolism of the trabecular meshwork; Invest. Ophthalmology & Visual Sci.; 20:625–31; (May 1981).
P.J. Anderson et al.; Metabolism of calf trabecular (reticular) meshwork; Invest. Ophthalmology & Visual Sci.; 19:13–20; (Jan. 1980).
M.G. Kahn et al.; Glutathione in Calf Trabecular Meshwork and its Relation to Aqueous Humor Outflow Facility; Invest. Ophthalomology & Visual Sci.; 24:1283–87; (Sep. 1983)

(List continued on next page.)

*Primary Examiner*—Zohreh Fay
*Attorney, Agent, or Firm*—Nixon & Vanderhye P.C.

[57] ABSTRACT

A method of increasing aqueous humor outflow in the eye of a human patient to treat glaucoma, the method comprising topically administering to the eye an outflow-increasing amount of an analog of ethacrynic acid having a margin of safety of at least 2.0 and having the formula wherein each $X_1$ and $X_2$, independently, is a halogen, H, or $CH_3$, or $X_1$ and $X_2$ together form a substituted or unsubstituted aromatic ring; $X_3$ is an organic group; and $X_4$ is OH or an organic group; provided that where $X_1$ and $X_2$ are Cl and $X_4$ is OH, $X_3$ cannot be 2-methylene-1-oxobutyl; or a pharmaceutically acceptable salt thereof.

3 Claims, No Drawings

OTHER PUBLICATIONS

D.R. Scott et al.; Glutathione Peroxidase of Calf Trabecular Meshwork; Invest. Ophthalmology Visual Sci.; 25:599–602; (May 1984).

T.F. Freddo et al.; Influence of Mercurial Sulfhydryl Agents on Aqueous Outflow Pathways in Enucleated Eyes; Invest. Ophthalmology & Visual Sci.; 25:278–85; (Mar. 1984).

D.L. Epstein et al.; The Biochemistry of Outflow Mechanisms; Applied Pharmacology in the Medical Treatment of Glaucomas; (Aug. 1984); 135–150.

D.L. Epstein; Open Angle Glaucoma; Arch Ophthalmol; 105:1187–88; (Sep. 1987).

D.L. Epstein et al.; Influence of Ethacrynic Acid on Outflow Facility in the Monkey and Calf Eye; Arvo paper; (May 1986).

D.L. Epstein et al.; Paracellular Outflow Routes Through The Inner Wall of Schlemm's Canal in Cynololgus Monkeys; Arvo Abstract; (1988).

R.R. Ozment et al.; The Effect of Intracameral Ethacrynic Acid on Intraocular Pressure of Living Monkeys; Arvo Abstract; (1988).

J.D. Peczon et al.; Diuretic Drugs in Glaucoma; American Journal of Ophthalmology; 64:680–83.

T. Guenther et al.; Specificity of ethacrynic acid as a sulfhydryl reagent; Pharmacodynamics; 84:99192h; p. 23; (1976).

D.A. Koechel; Diuretic activity of Mannich base derivatives of ethacrynic acid and certain ethacrynic acid analogs; Chemical Abstracts; 89:53289; (1978).

E.J. Cargoe Jr. et al.; (1–Oxo–2–halo–5–indanyloxy)alkanoic acids; Chemical Abstracts; 82:170484.

E.J. Cragoe Jr. et al.; Diuretic and saluretic 1–oxo–2–alkylidene–5–indanyl–oxy(thio)acetic acids; Chemical Abstracts; 73:25182f; (1970).

E.J. Cragoe Jr. et al.; Diuretic and saluretic substituted (1–oxoinden–5–yl–oxy)acetic acids; Chemical Abstracts; 73:25181e; (1970).

E.J. Cragoe Jr. et al.; Antiinflammatory 3,4–dihydro–2H–pyran; Heterocyclic Compounds; 71:91305h.

E.J. Cragoe Jr. et al.; $\alpha[(\alpha\text{Methylenealkanoyl)phenoxy}]$ alkanoic acids; Chemical Abstracts; 71:70324y; (1969).

Merck & Co., Inc.; 2–(Hydrocarbylpolythiomethyl)alkanoyl phenoxy–acetic acids; Chemical Abstracts; 66:104824a; (1967).

INCREASING AQUEOUS HUMOR OUTFLOW

BACKGROUND OF THE INVENTION

This Application is a continuation of application Ser. No. 08/152,248, filed Nov. 12, 1993, now abandoned, which is a continuation of application Ser. No. 08/028,631 filed Mar. 5, 1993, now abandoned, which is a continuation of application Ser. No. 07/908,636, filed Jun. 11, 1992, now abandoned, which is a continuation of application Ser. No. 07/747,461 filed Aug. 12, 1991, now abandoned, which is a continuation of application Ser. No. 07/514,488, filed Apr. 26, 1990, now abandoned, which is a continuation-in-part of application Ser. No. 07/123,797, filed Nov. 23, 1987, now abandoned, which is a continuation-in-part of application Ser. No. 06/745,325, filed Jun. 14, 1985, now abandoned.

This invention relates to the treatment of disorders of the human eye, particularly glaucoma.

Glaucoma is characterized by intraocular pressure resulting at least in part from a diminished outflow of aqueous humor through the trabecular meshwork.

Epstein et al. (1982) Invest. Ophthalmol. Vis. Sci. 22, 6, 752–756 describes experiments in which eyes from dead calves, macaques, and baboons were fitted with stainless-steel corneal fittings. The eyes were perfused, by filling the anterior chambers at 15 mm Hg and 22° C., with a solution containing the toxic compound N-ethylmaleimide (NEM), a compound reactive with sulfhydryl groups. It was found that a "dosage of NEM of 4.7 mM or greater produced a significant increase in the facility of outflow in the calf eye." "NEM also caused an increase in outflow in the monkey eye." The paper goes on:

> Our results indicate that chemical modification of cellular —SH groups can also alter the egress of aqueous humor from the trabecular meshwork. Cellular or intercellular permeability to fluid flow in the aqueous outflow channels may be influenced by the state of cell membrane protein sulfhydryls. Trabecular —SH groups may be intimately involved in the normal process of aqueous outflow, especially if located at sites of normal resistance in the juxtacanalicular tissue or endothelium of Schlemm's canal. Alternatively, —SH groups may exert only a secondary influence on outflow through nonspecific structural changes in trabecular cell membranes.

SUMMARY OF THE INVENTION

In general, the invention features a method of increasing aqueous humor outflow in the eye of a human patient to treat glaucoma, which method comprises topically administering to the eye an outflow increasing amount of analogs of ethacrynic acid and their ester or amide derivatives, and pharmaceutically acceptable salts thereof, having a margin of safety of at least 2.0 and being of the general formula

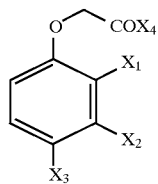

wherein each $X_1$ and $X_2$, independently, is a halogen, H, or $CH_3$, or $X_1$ and $X_2$ together form a substituted or unsubstituted aromatic ring; $X_3$ is an organic group, preferably, a sulfhydryl reactive organic group; and $X_4$ is OH or an organic group; provided that where $X_1$ and $X_2$ are Cl and $X_4$ is OH, $X_3$ cannot be 2-methylene-1-oxobutyl; and where, preferably, each $X_1$ and $X_2$, independently, is H, Cl, $CH_3$, or $X_1$ and $X_2$ together form a phenyl ring; and $X_3$ is one of

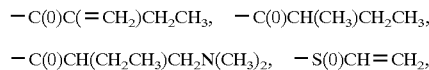

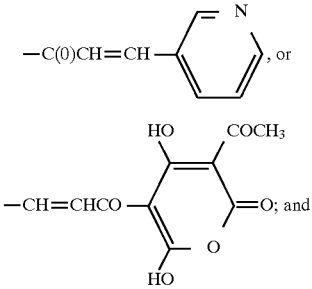

$X_4$ is one of OH,

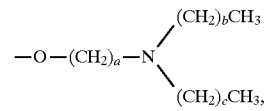

$-O-(CH_2)_a-CH(OH)CH_2OH$, and

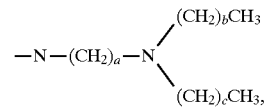

wherein a is 2–20, and b and c are, independently, 0–20.

The invention provides effective, non-surgical treatment of glaucoma in a manner which increases fluid outflow while causing minimal non-fluid related ocular functions.

Other features and advantages of the invention will be apparent from the following description of the preferred embodiments thereof, and from the claims.

DESCRIPTION OF THE PREFERRED EMBODIMENTS

As mentioned above, the compounds useful in the methods of the invention have a number of required properties, now discussed in greater detail.

Reactivity

Compounds of the invention are reactive with the trabecular meshwork so as to increase aqueous humor outflow; some are reactive with sulfhydryl groups of the trabecular meshwork. The reactivity of the compounds must not cause an unacceptable amount of swelling of the cells of the trabecular meshwork, particularly the inner wall endothelial cells of Schlemm's canal, because swelling can decrease outflow. "Unacceptable amount of swelling", as used herein, means an amount of swelling which completely counteracts the outflow increasing effects of the compounds, resulting in no net outflow increase. Whether swelling is caused by a particular compound can be determined by testing the compound in the system described in Epstein et al., id, and examining the trabecular meshwork cells morphologically.

Sulfhydryl Reactivity

The compounds may contain chemical groups which are capable of reacting with the sulfhydryl groups of the trabecular meshwork to increase aqueous humor outflow. Compounds which contain chemical groups capable of reacting with sulfhydryl groups must react with the sulfhydryl groups in a manner which does not cause an unacceptable amount of swelling of cells of the trabecular meshwork, as described above.

Suitable sulfhydryl reactive groups include C=C, C=O, sulfhydryl, alkyl (e.g., methyl or ethyl) and aryl (e.g., phenyl) substituted with a good leaving group, e.g., halogen, tosyl, or mesyl. Preferably, in the case of substituted alkyl groups, substitution is primary, rather than secondary or tertiary, for greater reactivity.

Toxicity and Margin of Safety

As used herein, "margin of safety" refers to the ratio of the dosage of the outflow increasing compounds which causes medically unacceptable toxic side effects, and the dosage which causes substantial (i.e., medically useful) increase in aqueous humor outflow in a typical human patient with advanced open angle glaucoma. The margin of safety of the compounds must be at least 2.0, and more preferably at least 4.0.

It is also important that the compounds not produce, at effective dosages, long-term deleterious changes in the eye.

Lipophilicity

Compounds to be administered to the eye topically must be sufficiently lipophilic to penetrate the corneal membrane. Sufficient lipophilicity can be provided by a non-polar structure, the presence of at least one aryl group (e.g., a substituted or unsubstituted phenyl ring), at least one halogen atom, and/or hydrophobic alkyl groups. For lipophilicity, it is also desirable that the compound not carry excessive charge; i.e., of absolute value greater than 2, at physiological pH.

Lipophilicity is expressed in terms of octanol: water coefficient, determined by the standard technique of radio-labelling the compound and introducing a small amount into equal volumes of octanol and Tris buffer (50 mM, pH 7.4). The coefficient of the compounds is preferably at least 0.005, and more preferably at least 0.01.

Administration

The outflow-increasing compounds can be administered either topically or by microinjection into the anterior chamber or trabecular meshwork. For topical administration, the compound is dissolved in a pharmaceutically acceptable carrier substance, e.g., physiological saline. For compounds having limited water solubility (e.g., the sodium salt of ethacrynic acid, soluble only to about 0.04M in water) the liquid carrier medium can contain an organic solvent, e.g., 3% methyl cellulose, in which solubility is greater. Methyl cellulose also provides, by its high viscosity, increased contact time between the compound and the eye surface, and therefore increased corneal penetration. Corneal penetration can also be increased by administering the compound mixed with an agent which slightly disrupts the corneal membrane, e.g., 0.001% benzalkonium chloride. Administration is by periodically (e.g., one time per week to ten times per day) applying drops of the compound in solution using an eye dropper, such that an effective amount of the compound is delivered through the cornea to the trabecular meshwork. The amount of the compound to be delivered in one administration will depend on individual patient characteristics, e.g., severity of disease, as well as characteristics of the compound, e.g., the specific affinity for trabecular meshwork sulfhydryl groups, and the magnitude of the margin of safety. Typically, each drop contains 50–100 microliters of a 5–10 mM solution of the compound, so that 0.025 to 0.10 moles of the compound are delivered to each eye per day.

Direct microinjection of the solubilized compound into the anterior chamber or trabecular meshwork offers the advantage of concentrating the compound in the location where it is needed, while avoiding the possibility of side effects resulting from generalized exposure of the eye to the compound. Microinjection also provides the advantage of permitting infrequent periodic administration, e.g., every few weeks, months, or even years, in contrast to the more frequent administrations required in the case of topical administration. Also, direct microinjection may promote the washing out of the trabecular meshwork of extracellular material interferring with fluid outflow. Dosage for microinjection, like that for topical administration, varies with the above-mentioned parameters. Typically, microinjection dosage is such that a final concentration of the compound within the anterior chamber or trabecular meshwork of 0.01 to 1.0 mM is reached.

In Vivo Use of Ethacrynic Acid

Ethacrynic acid (sodium salt) was used to increase aqueous humor outflow in cynomologous monkeys, as described below. Ethacrynic acid can be purchased from Merck, Sharp, and Dome, and is described in U.S. Pat. No. 3,255,241, hereby incorporated by reference. Ethacrynic acid has the chemical formula [2,3-dichloro-4-(2-methylene-1-oxobutyl) phenoxy] acetic acid. Any suitable analog described in U.S. Pat. No. 3,255,241 or its ester or amide derivative can also be used as described herein; for example, the following compounds may be used and are available from Allergan, Inc. (Irvine, Calif.), as indicated by the code number below the structure.

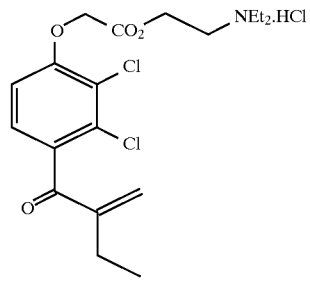

AGN 190557-A

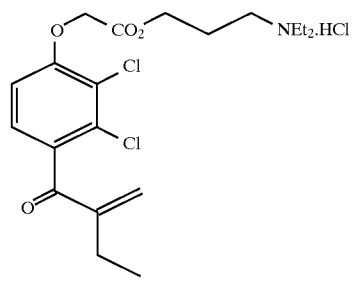

AGN 190558-A

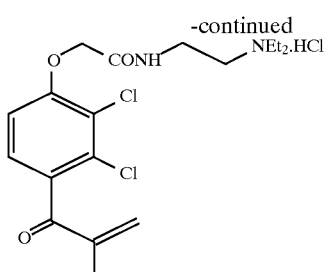

AGN 190553-A

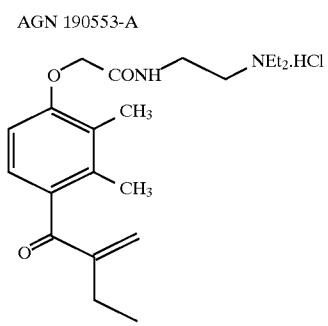

AGN 190552-A

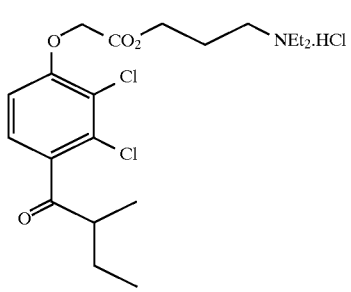

AGN 190557-A

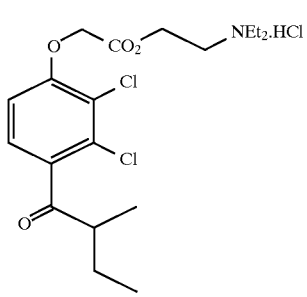

AGN 190558-A

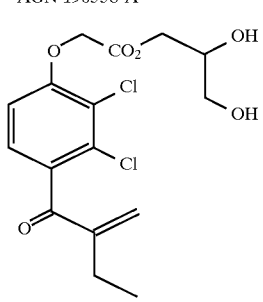

AGN 190435

Each animal was randomly assigned one eye for the experimental and the other for its control perfusion. The animals were fasted the night before the experiment. They were anesthetized intramuscularly with Methohexital Sodium 15 mg/kg and Pentobarbital Sodium 35 mg/kg. Supplemental anesthesia as required was carried out with Pentobarbital 10 mg/kg/hour. Needles were placed through the cornea into the anterior chamber and a two-step constant pressure perfusion method was performed in order to determine aqueous humor outflow facility. The basic medium for perfusion was Dulbecco's phosphate buffered saline with added 5.5 mM glucose. A 10 microliter bolus of the experimental or control solution (that would produce the desired final concentration in the anterior chamber) was injected through a T shaped connector piece in the infusion line.

Each vial of ethacrynic acid contained ethacrynate sodium powder equivalent to 50 mg of ethacrynic acid. The inactive ingredients were 62.5 mg mannitol and 0.1 milliliters thimerosol (as preservative). The powder was diluted with the above basic medium (Dulbecco's with added glucose) to yield the desired concentration. The solution was mixed at room temperature until dissolved, and the pH was determined (always 7.2) before use; the solution was filtered with a 0.2 micron filter (Nuclepore); this produced a solution which was stable for 24 hours.

The control solution was composed of 9.5 mg sodium chloride (to osmotically balance the experimental solution), 62.5 mg mannitol and 0.1 milliliter thimerosol dissolved in Dulbecco's phosphate buffered saline with 5.5 mM added glucose to yield the desired concentration.

During perfusion experiments, a 10 microliter bolus injection was made using a Hamilton syringe. Since the monkey anterior chamber is approximately 200 microliters, 10 microliters of 10 mM ethacrynic acid was infused to achieve a final concentration of 0.5 mM ethacrynic acid.

Experiments were carried out using final ethacrynic acid concentrations in the aqueous humor of 0.1 mM to 0.5 mM. There were at least three animals and separate experiments carried out for each of the concentrations 0.1 MM, 0.25 mM, and 0.5 mM.

At 0.5 mM, a mean increase in fluid outflow facility of 140% due to ethacrynic acid was determined, compared to no change in the control perfused eye. At 0.25 mM, approximately half the animals perfused responded with a substantial increase in outflow facility due to ethacrynic acid and the other half did not. At lower dosages there was no effect. One animal was perfused at 1.0 mM and demonstrated a 355% increase in the experimental eye compared to an 18% increase in the control eye.

There were no apparent corneal or crystalline lens changes. Specifically, there was no chronic corneal edema or opacities or cataract formation. At dosages above 0.25 mM some of the animals developed a dilated pupil in the ethacrynic treated eye. A small number of animals in both the experimental and control eyes developed adhesions of the iris to the peripheral cornea which was believed to result from the perfusion technique itself rather than the drug administration.

Intraocular pressure could not be reliably taken until a few days after the perfusion experiments (due to the possibility of leaks in the cornea through the needle placements), and at that time intraocular pressure was symmetrical and normal in both eyes.

For rabbit experiments Dutch-belted rabbits of either sex weighing 1.5 to 2 kg were used for topical studies. Each animal was randomly assigned one eye for the experimental and the other for its control solution. Intraocular pressure was measured using a Digilab Pneumotonometer. Any animals showing asymmetry of intraocular pressure greater than 2 mm were excluded form the study.

The protocol was as follows. Baseline intraocular pressure was taken in each eye using 0.5% proparacaine hydrochloride for topical anesthesia. Then a 100 microliter drop of either control solution or ethacrynic acid dissolved in 3% methylcellulose (Dow Corporation, lot number 14728) was instilled into one of the two eyes. In a half hour this was repeated. Two hours later intraocular pressure was measured in each eye. In some animals intraocular pressure was also measured five hours later and all animals had measurement of intraocular pressure the following day.

Ethacrynic acid powder was dissolved in 3% methylcellulose to yield the desired concentration. The solution was mixed at room temperature for one hour and was stable for 24 hours. A similar osmotically balanced control solution was prepared from methyl cellulose powder dissolved in distilled water using low heat for several hours. The solution was refrigerated over night to yield a transparent, viscous fluid. The pH of the solution was determined by mixing one part of the control or experimental solution with five parts of distilled water. The pH ranged between 6.2 and 6.5 for both the control and experimental solutions. The 3% methylcellulose solution was refrigerated when not in use.

The pressure data was as follows: for 5 mM ethacrynic acid in 3% methylcellulose in eight animals, two hours following instillation intraocular pressure in the ethacrynic treated eye had decreased from 22.4 to 19.6 mm Hg (p less than 0.01) whereas the control eye had shown a slight increase from 21.5 to 23.1 mm Hg. The next day intraocular pressure was equal in the two eyes being 22.4 mm in the ethacrynic treated eye and 22.7 mm in the control eye.

In fourteen rabbits treated with 10 mM ethacrynic acid and 3% methylcellulose, 24 hours after instillation intraocular pressure in the ethacrynic eye had changed from 23.0 to 20.0 mm Hg whereas in the control eye it had changed from 22.9 to 24.2 mm Hg. p was less than 0.001.

For studies at 5 mM concentration, there was slight conjunctival infection following administration. There were no other side effects noted. Following administration of 10 mM ethacrynic acid moderate conjunctival infection and signs of irritation were apparent.

At higher concentrations signs of corneal toxicity (corneal edema) and anterior chamber inflammation were apparent for several days. However, these resolved without apparent sequelae.

In vitro experiments with excised mammalian eyes indicated that the following ethacrynic acid analogs (available from Allergan, Inc.) increased aqueous humor outflow in the eyes:

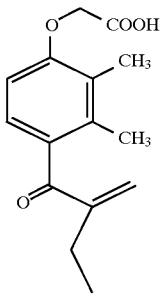

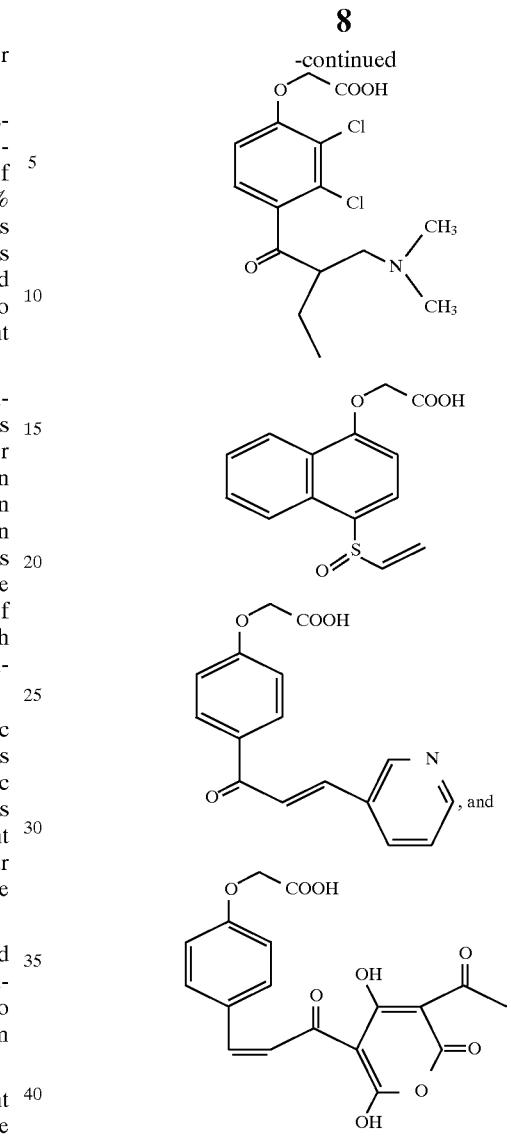

Experiments similar to those described above have also been performed using two esters of ethacrynic acid, RCOOCH$_2$CH$_2$N(CH$_2$CH$_3$)$_2$ (hereinafter "ester A") and RCOOCH$_2$CH$_2$CH$_2$N(CH$_2$CH$_3$)$_2$ (hereinafter "ester B"), where R is [2,3-dichloro-4-(2-methylene-1-oxobutyl) phenoxy]acetate.

After topical application of 10 mM ester A, a reduction in intraocular pressure in the rabbit was observed. This was most apparent 24 hours after instillation (control eye intraocular pressure changing from 22±3 to 15±2 mm Hg; n=8). In all these topical experiments 2 drops of the agent were given 5 minutes apart and control eyes were fully sham manipulated. Most of the animals demonstrated some irritation of the eyelid and a few to the conjunctiva and nictitating membrane, but no corneal changes were observed. However, not all the animals were slit lamped. No anterior chamber inflammation was observed that might explain the pressure decrease, and the external irritation of the lid seemed to clear after 24 hours. In the two rabbits studied at 5 mM ester A, minimal if any irritation was observed.

For 10 mM ester B in the rabbit, a pressure reduction only at 24 hours was apparent with control eyes changing from 24±2 to 24±2 mm Hg and experimental eyes from 23±3 to 15±3 mm Hg (n=5). Similar signs of external irritation to the lid and conjunctiva were apparent with ester B, but probably less than with ester A. At 24 hours there were clearly only minimal if any signs of irritation and there were no slit lamp observations of ocular inflammation that might explain the significant pressure reduction observed at 24 hours.

In the monkey, a significant pressure reduction 24 hours after application of 10 mM ester A was observed (control eyes changing from 17±3 to 21±2 mm Hg versus experimental eyes changing from 19±1 to 5±3 mm Hg; n=6). However, significant corneal edema was also observed in over half of the monkeys. This was detected by flashlight examination and confirmed by slit lamp examination. The corneal edema ultimately resolved in all animals. At 5 mM topical ester A in the monkey, corneal edema was likewise apparent and no pressure reduction was documented.

Other embodiments are within the following claims.

I claim:

1. A method of increasing aqueous humor outflow in the eye of a human patient to treat glaucoma, said method comprising topically administering to said eye an outflow increasing amount of an analogue of ethacrynic acid having a sulfhydryl reactive group reactive with the trabecular meshwork of the eye to increase aqueous humoral outflow.

2. The method of claim 1 wherein the sulfhydryl reactive group of the ethacrynic acid analogue is selected from the group consisting of C=C, C=O, sulfhydryl, an alkyl and an aryl substituted with a leaving group.

3. The method of claim 2 wherein said leaving group is a halogen, tosyl or mesyl group.

* * * * *